US006503211B2

(12) United States Patent
Frye

(10) Patent No.: US 6,503,211 B2
(45) Date of Patent: Jan. 7, 2003

(54) PNEUMATIC SPINAL AND EXTREMITY MANIPULATOR

(76) Inventor: Bruce A. Frye, 3126 S. Garnett, Suite H, Tulsa, OK (US) 74146

( * ) Notice: Subject to any disclaimer, the term of this patent is extended or adjusted under 35 U.S.C. 154(b) by 0 days.

(21) Appl. No.: 09/865,343

(22) Filed: May 25, 2001

(65) Prior Publication Data

US 2002/0177795 A1 Nov. 28, 2002

(51) Int. Cl.[7] .................................................. A61M 1/00
(52) U.S. Cl. ........................................ 601/107; 601/108
(58) Field of Search ............................... 601/78–80, 97, 601/105, 107, 108; 606/237–239

(56) References Cited

U.S. PATENT DOCUMENTS 2,421,354 A 5/1947 Reiter
2,970,592 A * 2/1961 David ........................ 601/107
3,894,586 A * 7/1975 Lyon .......................... 173/135
3,955,563 A 5/1976 Maione
4,016,873 A 4/1977 Anderson
4,461,286 A 7/1984 Sweat
4,498,464 A 2/1985 Morgan, Jr
4,669,454 A 6/1987 Shamos
4,682,490 A 7/1987 Adelman et al.
4,716,890 A 1/1988 Bichel
4,841,955 A 6/1989 Evans et al.
5,160,336 A * 11/1992 Favre ......................... 601/108
5,626,615 A 5/1997 Keller et al.

* cited by examiner

*Primary Examiner*—Justine R. Yu
(74) *Attorney, Agent, or Firm*—Leydig, Voit & Mayer, Ltd.

(57) ABSTRACT

A pneumatically operated chiropractic thruster or manipulator that has a gun shaped body including an upper barrel and lower handle wherein the thrust element is free to move inwardly when depressed against a human body to accomodate automatically different stroke lengths, and the force delivered is adjustable by changing air pressure at the thruster by a rotable needle valve knob control having a predetermined number of indicated settings. The thruster can be operated with a single or a multiple thrust mode upon a single depression of a valve activator trigger.

7 Claims, 3 Drawing Sheets

PNEUMATIC SPINAL AND EXTREMITY MANIPULATOR

CROSS-REFERENCE TO RELATED PATENT APPLICATIONS

This patent application is based in part on Disclosure Document No. 481,929, filed Oct. 31, 2000.

FIELD OF THE INVENTION

The present invention relates generally to a pneumatic chiropractic thruster for use in chiropractic adjustment of musculoskeletal structures. More, particularly, this invention concerns an improved pneumatically operated chiropractic-adjusting device for use in spinal manipulative therapy to apply impact forces or thrusts to a human body.

BACKGROUND OF THE INVENTION

DESCRIPTION OF THE PRIOR ART

The chiropractic art is generally concerned with adjusting misaligned body structures by manually manipulating the various joints in the human body. Of more specific interest in the art, however, is the spinal column which is comprised of several interconnected musculoskeletal structures or vertebrae. Unlike other, less critical body structures, the spinal column must be treated or manipulated with extreme caution because of its link with the central nervous system.

The human spine is susceptible to many different pathologic abnormalities including misalignment, miscellaneous trauma and pain, and degeneration as a result of age or disease. By employing various physical therapy techniques, though, a chiropractor, or one skilled in the chiropractic art, may be able to successfully treat a pathologic spine. Successful treatment will not only relieve any pain or discomfort that the patient might be suffering, but will also improve the overall quality of life of that patient.

One common spinal-adjustment technique involves applying thrusts or forces to the afflicted region of the spine. In particular, this technique involves either "mobilizing" the spine (i.e. passively moving the spine with relatively slow cyclic or oscillatory motion), or "manipulating" the spine (i.e. applying an impulsive thrust or force in a well-defined direction to a specific region of the spine). Depending on professional affiliations, this technique is referred to as chiropractic adjustment, osteopathic manipulation, orthopedic manual therapy, and/or spinal manipulative therapy.

There are several well-known procedures or techniques for "manipulating" or administering impulsive thrusts to a spine. One technique involves applying one or more rapid thumb thrusts to misaligned or afflicted vertebrae. Thumb thrusts, however, tend to be both imprecise in magnitude and location and tiresome to administer. Another technique involves using a manually operated chiropractic-adjusting instrument. For instance, U.S. Pat. No. 4,116,235, issued to Fuhr et al. ("Fuhr") and U.S. Pat. No. 4,498,464, issued to Morgan, Jr., disclose such instruments.

Throughout the years it has also been known that power driven devices at times can offer benefits or advantages in use over the manually operated devices.

Electric solenoid operated adjustors such as ones described in Evans U.S. Pat. No. 4,841,955 issued in 1989 or Adelman U.S. Pat. No. 4,682,490, issued in 1987, can provide adjusting and controllability benefits over manual devices. However, using an electrical appliance close to the body can be potentially hazardous and even prohibited by governmental regulatory agency rules or regulations.

Thus, numerous efforts have been made to develop a pneumatically operated thruster with all of the desired features and benefits required for safe and varied usage of such devices. Examples of such an approach in pneumatic operated thrusters is shown in U.S. Pat. No. 4,716,890, issued in 1988 to Bichel and references cited in the Bichel patent.

While the Bichel thruster as described did seek to overcome disadvantages presented in prior art devices, it still did not provide certain features and advantages required to achieve wide spread acceptance and use by chiropractic practitioners.

By way of example, it may be noted that such prior devices including Bichel are capable of only delivering a single thrust or stroke, provide only manual adjustability of stroke lengths; provide force adjustment by changing stroke length and change air pressure only at the compressor or supply source. In addition they involve complicated multiple parts designs which make them more costly to manufacture and more difficult and costly to maintain or use.

BRIEF SUMMARY OF THE INVENTION

The present invention provides a pneumatic chiropractic thruster or manipulator for use in chiropractic treatment to apply controlled impact forces or thrusts to a human body wherein a resilient tipped thrust element automatically adjusts itself for stroke length and force applied by an air pressure driven piston member can be conveniently changed at the thruster by changing the air pressure with a rotatable control having predetermined settings. The thruster can also deliver multiple as well as single strokes with a single push of a valve trigger. The thruster has been simplified as its parts and components to lower the costs and render it simpler to use, adjust and service or maintain.

Other objects, features and advantages of the invention will become apparent upon reading the following description of a preferred exemplified embodiment of the invention and upon reference to the accompanying drawings.

While the invention will be described and disclosed in connection with a certain preferred embodiment, it is not intended to limit the invention to a specific embodiment. Rather, it is intended to cover all such alternative embodiments and modifications as full within the spirit and scope of the appended claims.

DETAILED DESCRIPTION OF THE INVENTION

Figure 1:
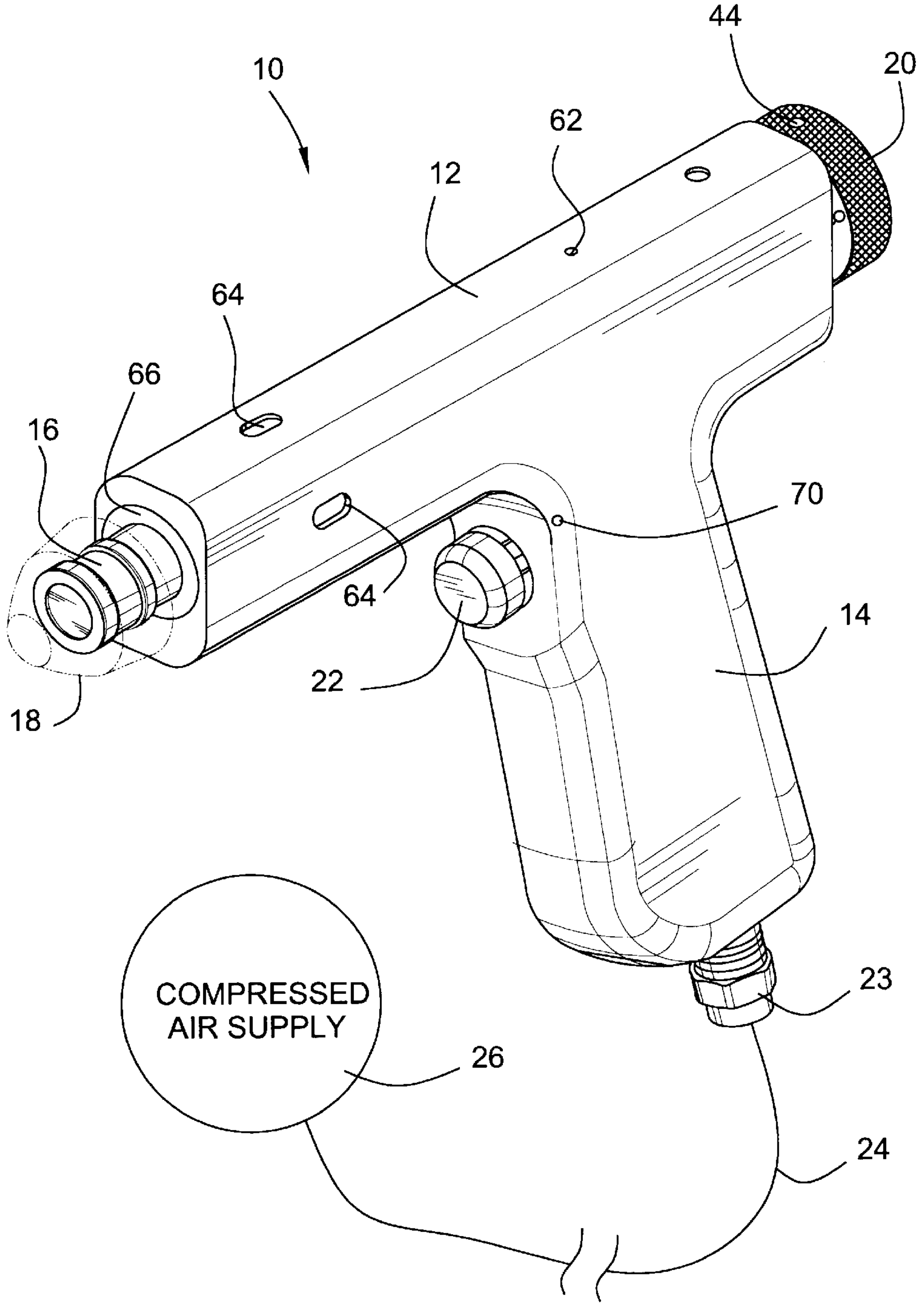
FIG. 1 is a side perspective view of an improved pneumatic chiropractic thruster or manipulator with automatic stroke length adjustment and air pressure adjustability at the thruster.

Referring now specifically to the drawings, FIG. 1 depicts an improved pneumatic chiropractic manipulator or thruster 10 in accordance with the present invention. The thruster 10 has a "gun-shaped" body with an upper barrel portion 12 and a lower handle portion 14.

A thrust element 16 protrudes from the forward end of barrel 12 and it is adapted to receive a removable, resilient tip 18. The tip 18 may be made of rubber or plastic and it can be interchangeable with different degrees of softness, hardness or durometer ratings as desired.

The rear end of the barrel 12 carries a pressure adjuster 20 in the form of a knurled knob controller.

At the upper forward portion of handle 14 there is provided a valve plunger or trigger 22. The lower end of the handle 14 receives a fitting 23 for a supply hose 24 that connects to a compressed air supply 26.

The compressed air supply 26 may be a portable tank or a compressor with typical relief and pressure setting valves as well as other peripheral devices for supplying compressed air safely through a hose 24 of suitable length to the thruster hose fitting 23.

Figures 2, 3:
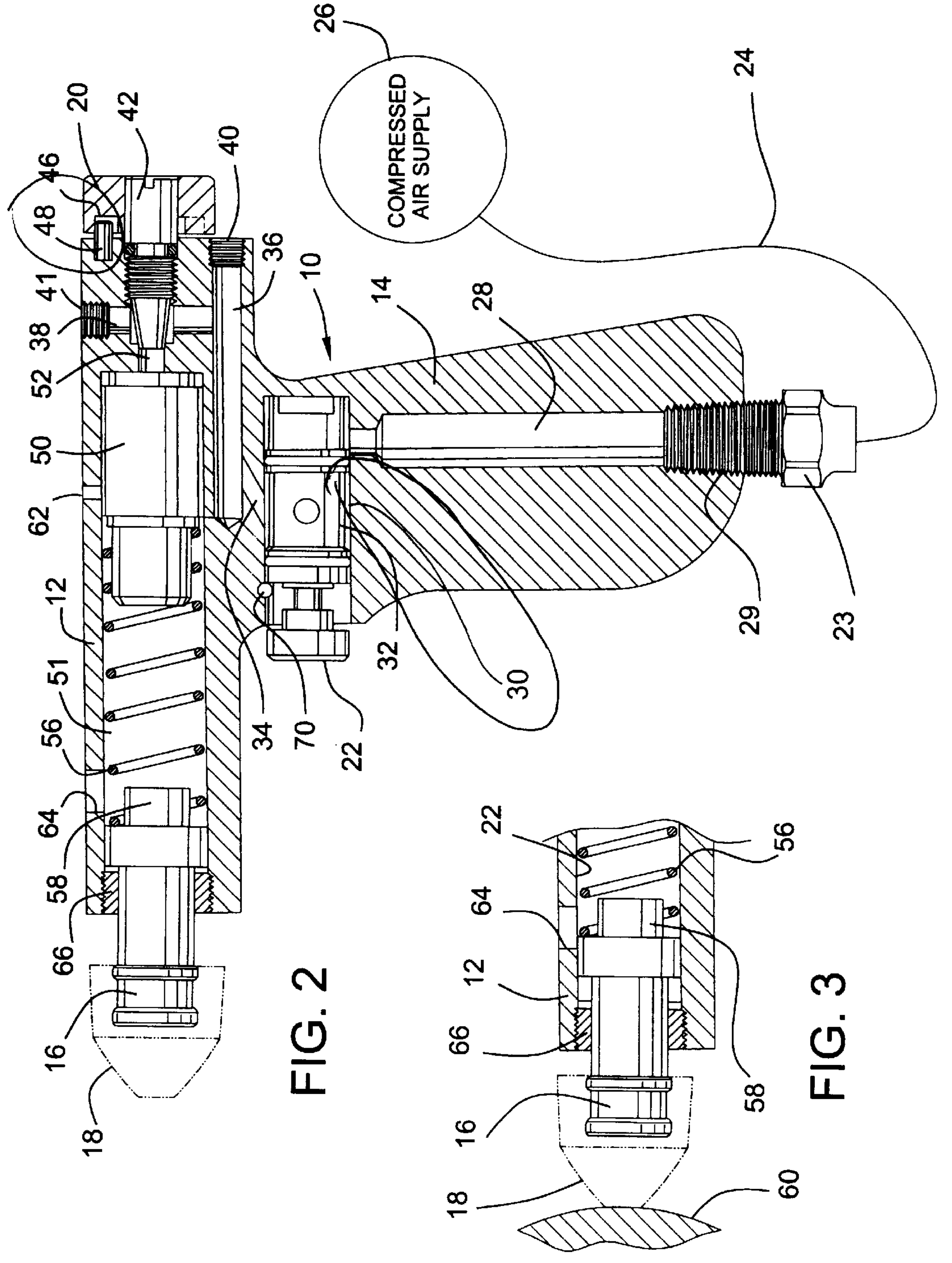
FIG. 2 is a cross sectional view of the thruster of FIG. 1.
FIG. 3 is a partial cross-sectional view of the thruster head portion showing its initial compression against a body.

As best depicted in FIG. 2, the handle 14 has a longitudinal bore 28, threaded at its lower end to receive the hose fitting 23. The longitudinal bore 28 connects to a horizontal bore 30 that receives trigger valve member 32. The arrangement is such that air supplied from compressed air supply 26 through the hose 24 is directed through bore 28 and contained until the trigger 22 is depressed. When trigger 22 is depressed, the air can then pass through port 34 into horizontal bore 36 in the barrel 12 and then to vertical bore 38. The bores 36 and 38 are closed by threaded plugs 40, 41, respectively.

Figure 4:
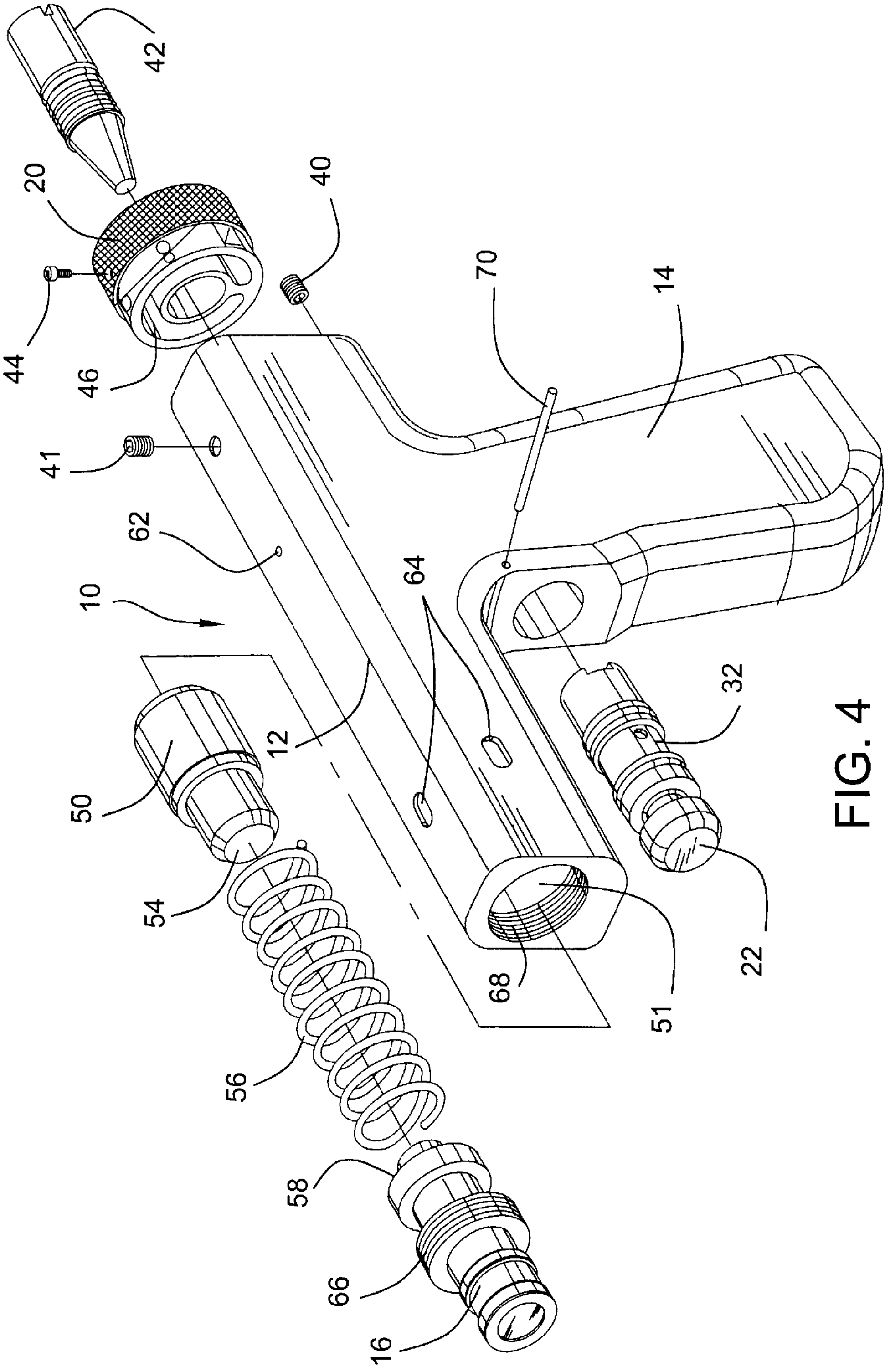
FIG. 4 is an exploded parts drawing showing the components of the thruster.

In accordance with one of the features of the present invention, air pressure delivered can be adjusted at the thruster itself and there is no need to then move to the air supplier for such adjustments. To accomplish this, the controller knob 20 carries a needle-valve 42 which can be selectively opened or closed by rotation of the knob. Preferably, the knob 20 is held to the needle valve 42 by a set screw 44 (FIG. 4) and the knob is provided with a predetermined number of indicated settings. An arcuate relief slot 46 in knob 20 coacts with a pin 48 to limit the rotation between the numbered or otherwise indicated settings.

In accordance with another important aspect of the present invention the stroke length is automatically determined to accommodate different areas of the body. For example, an area like the cervical spine has little muscle and fat so a thrust element does not travel forward very much before it returns or recoils. On the other hand, an area of a large person with a thick fat pad requires a longer stroke length and the thruster head moves further until reaching the vertebrae and hits an area sufficient to recoil. In other words, with a hard surface there is little or no travel distance for the thrust head while a soft thick surface has a longer thrust element movement.

Referring to FIG. 2, there is provided a piston member 50 that is driven forward in the barrel bore 51 by pressurized air allowed to enter behind the piston 50 through port 52 with the air pressure force being controllably adjusted with needle valve 42 as previously discussed.

In keeping with the present invention, when the trigger 22 is depressed air enters and drives the piston 50 forward until its forward end 54 overcoming the resistance of spring 56 strikes the rear anvil end 58 of thrust element 16. The thrust element 16, is free to move inwardly against the spring resistance initially so as shown in FIG. 3 pressing against a body 60 at the outset permits the thrust element to be moved inwardly changing the stroke length as discussed above.

The barrel has an exhaust port 62 which is positioned so that air pressure driving the piston 50 is relieved when the port is uncovered by passage of the piston. The placement of the exhaust port 62 restricts the forward translation of the thrust head since the build up of resistance and the force of the compressed spring 56 acts to then restore the piston back towards the rear end of the thruster. Ports 64 in the forward portion of barrel 12 avoid a pressure build up in front of the piston 50 as it travels forward.

The simplicity and ease of operating the thruster results since it has a minimal number of parts and it is easy to assemble, disassemble and operate. The thruster head element is held by a threaded sleeve 66 that goes into the threaded entry 68 of barrel bore 51. The trigger valve assembly 32 is held by a pin 70. Anvil end 58 of the thrust element 16 is preferably a hard plastic material to deaden impact sound giving the thruster a smooth and quiet operation.

In accordance with yet another of the features of the present invention, multiple thrusts are possible with the placement of the exhaust port 62 so that a single depression of the trigger and holding of it in allows the piston 50 to oscillate between covering and uncovering the port 62. Any recoil occurs at the thrust head end such that the thruster itself has little or no recoil back into the user's hand.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Of course, variations of those preferred embodiments will become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pneumatic chiropractic thruster adapted to be connected to a source of compressed air supply comprising in combination:

a body portion including a thruster head element carried in a horizontal bore within said body portion for biasing the head element;

said head element being freely moveable against one end of a spring biasing means within the body portion;

a piston reciprocally moveable within the body portion and acting against an opposite end of said spring biasing means;

a chamber behind the piston communicates with an air outlet port within the body;

said body having an air supply source bore with an inlet port;

trigger operated valve means carried by the body portion and located between the air inlet port and the outlet port for delivery of air from the source to the outlet port and the chamber upon operation of the valve means;

said outlet port being connected to the chamber behind said piston to receive the air supply and drive the piston forwardly towards and into contact with the head element; and an adjustable control valve interposed between the outlet port and chamber for selectively changing the amount of air under pressure supplied to drive the piston forward.

2. A thruster as claimed in claim 1 wherein the body portion is gun shaped and includes a barrel portion and a depending handle portion.

3. A thruster as claimed in claim 2 wherein the trigger operated valve is in the handle portion and the controller valve is in the barrel portion.

4. A thruster as claimed in claim 3 wherein the adjustable control valve is a needle valve and operated by a rotatable knob having predetermined position settings.

5. A thruster as claimed in claim 1 wherein the adjustable control valve is a needle valve rotatably adjustable by a control knob having predetermined position settings.

6. A thruster as claimed in claim 1 wherein said body portion has an exhaust port directed to the body portion bore and positioned to be uncovered upon passage of said piston toward said head element so as to relieve the air pressure driving of the piston and allowing it to be returned upon buildup of resistance from said biasing means thereby recovering said exhaust port.

7. A thruster as claimed in claim 6 wherein the exhaust port is positioned to allow multiple thrusts with a single actuation of said trigger valve means by way of said piston oscillating between covering and uncovering of said exhaust port.

* * * * *